United States Patent
Lynch et al.

(10) Patent No.: US 6,450,984 B1
(45) Date of Patent: Sep. 17, 2002

(54) SHUNT DEVICE AND METHOD FOR TREATING GLAUCOMA

(75) Inventors: Mary G. Lynch; Reay H. Brown, both of Atlanta, GA (US)

(73) Assignee: GMP Vision Solutions, Inc., Ft Lauderdale, FL (US)

( * ) Notice: Subject to any disclaimer, the term of this patent is extended or adjusted under 35 U.S.C. 154(b) by 0 days.

(21) Appl. No.: 09/558,505

(22) Filed: Apr. 26, 2000

Related U.S. Application Data

(60) Provisional application No. 60/131,030, filed on Apr. 26, 1999.

(51) Int. Cl.[7] .................................................. A61M 5/00
(52) U.S. Cl. ............................................. 604/8; 604/284
(58) Field of Search ........................ 604/8, 264, 284, 604/523; 606/107; 623/4.1, 1.1, 11.11, 1.35

(56) References Cited

U.S. PATENT DOCUMENTS

| 3,788,327 A | 1/1974 | Donowitz | 128/350 R |
| 4,037,604 A | 7/1977 | Newkirk | 128/350 V |
| 4,402,681 A | 9/1983 | Haas et al. | 604/9 |
| 4,428,746 A | 1/1984 | Mendez | 604/8 |
| 4,521,210 A | 6/1985 | Wong | 604/8 |
| 4,634,418 A | 1/1987 | Binder | 604/8 |
| 4,750,901 A | 6/1988 | Molteno | 604/8 |
| 4,787,885 A | 11/1988 | Binder | 604/8 |
| 4,886,488 A | 12/1989 | White | 604/9 |
| 4,936,825 A | 6/1990 | Ungerleider | 604/8 |
| 4,946,436 A | 8/1990 | Smith | 604/8 |
| 4,968,296 A | 11/1990 | Ritch et al. | 604/8 |
| 5,041,081 A | 8/1991 | Odrich | 604/9 |
| 5,073,163 A | 12/1991 | Lippman | 604/8 |
| 5,092,837 A | 3/1992 | Ritch et al. | 604/8 |
| 5,127,901 A | 7/1992 | Odrich | 604/9 |
| 5,178,604 A | 1/1993 | Baerveldt et al. | 604/8 |
| 5,180,362 A | 1/1993 | Worst | 604/8 |

(List continued on next page.)

FOREIGN PATENT DOCUMENTS

| CA | 2244646 | 2/1999 |
| CH | 92111244 | 7/1993 |
| DE | 198 40 047 A | 3/2000 |
| EP | 0 858 788 A1 | 8/1998 |
| EP | 0 898 947 A2 | 3/1999 |
| FR | 2710269 | 3/1995 |
| JP | HEI 11-123205 | 5/1999 |
| WO | WO 98/30181 | 1/1998 |
| WO | WO 98/23237 | 6/1998 |
| WO | WO 98/35639 | 8/1998 |
| WO | WO 99/26567 | 6/1999 |
| WO | WO 99/38470 | 8/1999 |
| WO | WO 00/13627 | 3/2000 |
| WO | WO 01/78631 | 10/2001 |
| WO | WO 01/78656 | 10/2001 |

OTHER PUBLICATIONS

Shields, M. Bruce, *Textbook of Glaucoma*, Fourth Ed., Williams & Wilkins Publishers, 1998, pp. 5–31.

*Biomedical Foundations of Ophthalmology*, vol. 1, Harper & Row Publishers, 1983, pp. 1–74.

(List continued on next page.)

*Primary Examiner*—Edward K. Look
*Assistant Examiner*—Richard A. Edgar
(74) *Attorney, Agent, or Firm*—Sutherland Asbill & Brennan

(57) ABSTRACT

Shunt devices and a method for continuously decompressing elevated intraocular pressure in eyes affected by glaucoma by diverting excess aqueous humor from the anterior chamber of the eye into Schlemm's canal where post-operative patency can be maintained with an indwelling shunt device which surgically connects the canal with the anterior chamber. The shunt devices provide uni- or bidirectional flow of aqueous humor into Schlemm's canal.

47 Claims, 6 Drawing Sheets

U.S. PATENT DOCUMENTS

| | | | |
|---|---|---|---|
| 5,300,020 A | 4/1994 | L'Esperance, Jr. | 604/9 |
| 5,318,513 A | 6/1994 | Leib et al. | 604/8 |
| 5,334,137 A | 8/1994 | Freeman | 604/8 |
| 5,338,291 A | 8/1994 | Speckman et al. | 604/9 |
| 5,346,464 A | 9/1994 | Camras | 604/9 |
| 5,360,399 A | 11/1994 | Stegmann | 604/49 |
| 5,370,607 A | 12/1994 | Memmen | 604/8 |
| 5,370,641 A | 12/1994 | O'Donnell, Jr. | 606/4 |
| 5,372,577 A | 12/1994 | Ungerleider | 604/8 |
| 5,397,300 A | 3/1995 | Baerveldt et al. | 604/8 |
| 5,433,701 A | 7/1995 | Rubinstein | 604/8 |
| 5,454,796 A | 10/1995 | Krupin | 604/294 |
| 5,476,445 A | 12/1995 | Baerveldt et al. | 604/8 |
| 5,486,165 A | 1/1996 | Stegmann | 604/8 X |
| 5,558,629 A | 9/1996 | Baerveldt et al. | 604/93 X |
| RE35,390 E | 12/1996 | Smith | 604/8 |
| 5,601,094 A | 2/1997 | Reiss | 604/8 X |
| 5,626,558 A | 5/1997 | Suson | 604/8 |
| 5,626,559 A | 5/1997 | Solomon | 604/9 |
| 5,681,275 A | 10/1997 | Ahmed | 604/9 |
| 5,702,414 A | 12/1997 | Richter et al. | 606/166 |
| 5,704,907 A | 1/1998 | Nordquist et al. | 604/8 |
| 5,713,844 A | 2/1998 | Peyman | 604/9 |
| 5,723,005 A | 3/1998 | Herrick | 604/8 X |
| 5,743,868 A | 4/1998 | Brown et al. | 604/8 |
| 5,752,928 A | 5/1998 | de Roulhac et al. | 604/8 |
| 5,766,243 A | 6/1998 | Christensen et al. | 623/4 |
| 5,785,674 A | 7/1998 | Mateen | 604/9 |
| 5,807,302 A | 9/1998 | Wandel | 604/8 |
| 5,830,171 A | 11/1998 | Wallace | 604/8 |
| 5,865,831 A | 2/1999 | Cozean et al. | 606/6 |
| 5,868,697 A | 2/1999 | Richter et al. | 604/8 |
| 5,879,319 A | 3/1999 | Pynson et al. | 604/8 |
| 5,882,327 A | 3/1999 | Jacob | 604/8 |
| 5,893,837 A | 4/1999 | Eagles et al. | 604/9 |
| 5,968,058 A | 10/1999 | Richter et al. | 606/166 |
| 6,050,970 A | 4/2000 | Baerveldt | 604/28 |
| 6,063,116 A | 5/2000 | Kelleher | 623/4 |
| 6,063,396 A | 5/2000 | Kelleher | 424/428 |
| 6,077,299 A | 6/2000 | Adelberg et al. | 604/9 X |
| 6,102,045 A | 8/2000 | Nordquist et al. | 604/8 X |
| 6,142,990 A * | 11/2000 | Burk | 606/17 |
| 6,168,575 B1 | 1/2001 | Soltanpour | 604/9 |
| 6,193,656 B1 | 2/2001 | Jeffries et al. | 600/398 |
| 6,197,056 B1 | 3/2001 | Schachar | 623/4.1 |
| 6,375,642 B1 | 4/2002 | Grieshaber et al. | 604/294 |
| 2002/0026200 A1 * | 8/2001 | Savage | 606/108 |

OTHER PUBLICATIONS

Buskirk, E. Michael et al., "Lens Depression and Aqueous Outflow in Enucleated Primate Eyes", American Journal of Ophthalmology, vol. 76, No. 5, Nov. 1973, pp. 632–640.

Buskirk, E. Michael et al., "Trabeculotomy in the immature, enucleated human eye", Invest. Ophthalmol. Visual Sci., vol. 6, No. 1, Jan. 1977, pp. 63–66.

Moses, Robert A. et al., "Blood Reflux in Schlemm's Canal", Arch Ophthamol., vol. 97, Jul. 1979, pp. 1307–1310.

Fine, Ben S., et al., "A Clinicopathologic Study of Four Cases of Primary Open–Angle Glaucoma Compared to Normal Eyes", American Journal of Ophthalmology, vol.91, No. 1, 1981, pp. 88–105.

Grierson, I., et al., "Age–related Changes in the Canal of Schlemm", Exp. Eye Res., (1984) 39, pp. 505–512.

McMenamin, Paul G., et al., "Age–related Changes in the Human Outflow Apparatus", Ophthalmology, vol. 93, No. 2., Feb. 1986, pp. 194–209.

Demailly, P., et al., "Non–penetrating deep sclerectomy combined with a collagen implant in primary open–angle glaucoma. Medium–term retrospective results", J. Fr. Ophthalmol., vol. 19, No. 11, 1996, pp. 659–666. (Abstract only).

*Glaucoma—Basic and Clinical Science Course,* Section 10, Chapter 11, 1998–1999, American Academy of Ophthalmology, p. 9.

Welsh, N.H., et al., "The 'deroofing' of Schlemm's canal in patients with open–angle glaucoma through placement of a collagen drainage device", Ophthalmic Surg. Lasers, vol. 29, No. 3, Mar. 1998, pp. 216–226, (abstract only).

Karlen, M.E., et al., "Deep sclerectomy with collagen implant: medium term results", Br. J. Ophthalmol. vol. 83, No. 1, Jan. 1999, pp. 6–11, (abstract only).

Hamard, P., et al., "Deep nonpenetrating sclerectomy and open angle glaucoma. Intermediate results from thbe first operated patients", J. Fr. Ophthalmol., vol. 22 (j), Feb. 1999, pp. 25–31, (abstract only).

Mermoud, A., et al., "Comparison of deep sclerectomy with collagen implant and trabeculectomy in open–angle glaucoma", J. Cataracat Refract. Surg., vol.25, No. 3, Mar. 1999, pp. 323–331, (abstract only).

Spiegel, Detlev, et al., "Schlemm's Canal Implant: A New Method to Lower Intraocular Pressure in Patients with POAG", Ophthalmic Surgery and Lasers, vol. 30, No. 6, Jun. 1999, pp. 492–494.

Johnson, M.C., et al, "The Role of Schlemm's Canal in Aqueous Outflow from the Human Eye", Investigative Ophthalmology & Visual Science, vol. 24, No. 3, Mar. 1983, pp. 320–325.

Wilson, Ellen D., "Implants offer choices for glaucoma surgeons", EW Glaucoma, Oct. 11, 1999, website "http://www.eyeorld.org/sep99/999p60.asp".

"Improving the flow: A survey of available implants", EW Practice Managment, Oct. 11, 1999, website "http://www.eyeworld.org/tooltime/999inserts.asp".

Samalonis, Lisa B., "New Horizons in the surgical treatment of glaucoma", EW Glaucoma, Oct. 11, 1999, website "http://www.eyeworld.org/sep99/999p62.asp".

U.S. Clinical Wick Trials, Oct. 11, 1999, website http://www.cornea.org/us.htm.

Allingham, R.R., et al., "Morphometric Analysis of Schlemm's Canal in Normal and Glaucomatous Human Eyes", Glaucoma Paper Presentation, (abstract only—not dated).

Robinson, James C., et al., "Superior Cervical Ganglionectomy: Effects on Aqueous Human Flow in the Cynomolgus Monkey", Glaucoma Paper Presentation, (abstract only—not dated).

Gharagozloo, N. Ziai, et al., "Unilateral exfoliation syndrome without glaucoma—a comparison of aqueous dynamica between affected and normal eyes", Glaucoma Paper Presentation, (abstract only—not dated).

Moses, Robert A., "Circumferential Flow in Schlemm's Canal", American Journal of Ophthalmology, vol. 88, No. 3, Part II, Sep. 1979, pp. 585–591.

Spiegel, D., "Surgical Glaucoma Therapy" in Benefits and Risks of Ophthalmological Therapy (Kampik & Grehn, Eds.) Ch. 7 (Germany 1998).

* cited by examiner

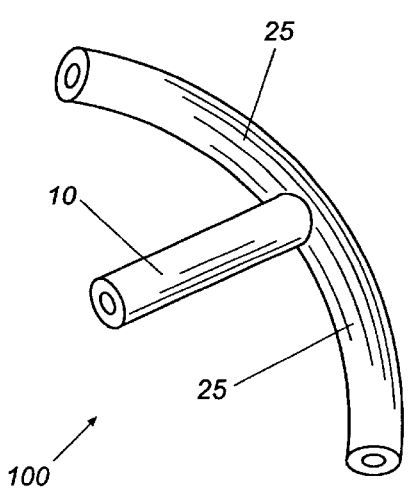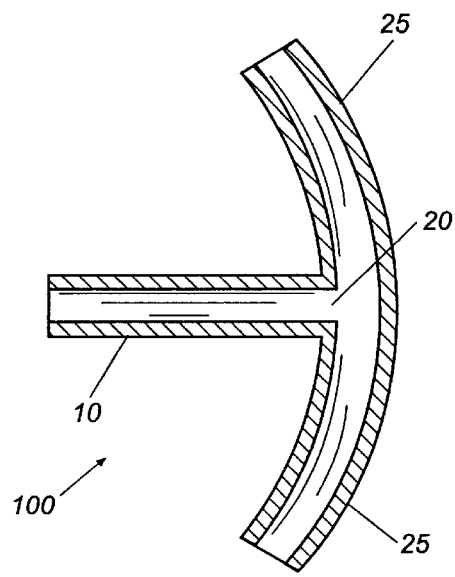
*Fig. 1A*  *Fig. 1B*
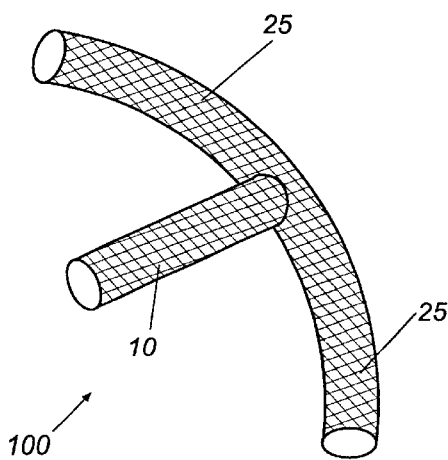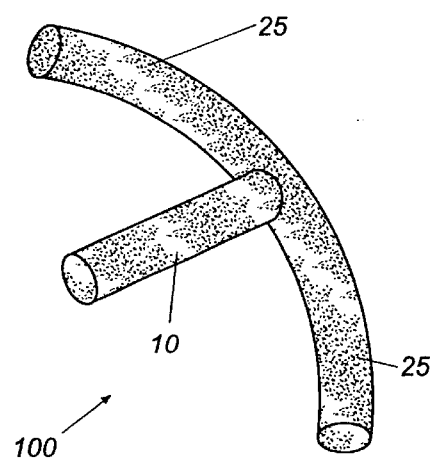
*Fig. 1C*  *Fig. 1D*

SHUNT DEVICE AND METHOD FOR TREATING GLAUCOMA

CROSS-REFERENCE TO RELATED APPLICATIONS

This application claims the benefit of U.S. Provisional Application No. 60/131,030, filed Apr. 26, 1999.

TECHNICAL FIELD

The present invention is generally directed to a surgical treatment for glaucoma, and relates more particularly to a device and method for continuously decompressing elevated intraocular pressure in eyes affected by glaucoma by diverting aqueous humor from the anterior chamber of the eye into Schlemm's canal where post-operative patency can be maintained with an indwelling shunt which can be surgically placed to connect the canal with the anterior chamber.

BACKGROUND OF THE INVENTION

Glaucoma is a significant public health problem, because glaucoma is a major cause of blindness. The blindness that results from glaucoma involves both central and peripheral vision and has a major impact on an individual's ability to lead an independent life.

Glaucoma is an optic neuropathy (a disorder of the optic nerve) that usually occurs in the setting of an elevated intraocular pressure. The pressure within the eye increases and this is associated with changes in the appearance ("cupping") and function ("blind spots" in the visual field) of the optic nerve. If the pressure remains high enough for a long enough period of time, total vision loss occurs. High pressure develops in an eye because of an internal fluid imbalance.

The eye is a hollow structure that contains a clear fluid called "aqueous humor." Aqueous humor is formed in the posterior chamber of the eye by the ciliary body at a rate of about 2.5 microliters per minute. The fluid, which is made at a fairly constant rate, then passes around the lens, through the pupillary opening in the iris and into the anterior chamber of the eye. Once in the anterior chamber, the fluid drains out of the eye through two different routes. In the "uveoscleral" route, the fluid percolates between muscle fibers of the ciliary body. This route accounts for approximately ten percent of the aqueous outflow in humans. The primary pathway for aqueous outflow in humans is through the "canalicular" route that involves the trabecular meshwork and Schlemm's canal.

The trabecular meshwork and Schlemm's canal are located at the junction between the iris and the sclera. This junction or corner is called "the angle." The trabecular meshwork is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal is adjacent to the trabecular meshwork. The outer wall of the trabecular meshwork coincides with the inner wall of Schlemm's canal. Schlemm's canal is a tube-like structure that runs around the circumference of the cornea. In human adults, Schlemm's Canal is believed to be divided by septa into a series of autonomous, dead-end canals.

The aqueous fluid travels through the spaces between the trabecular beams, across the inner wall of Schlemm's canal into the canal, through a series of about 25 collecting channels that drain from Schlemm's canal and into the episcleral venous system. In a normal situation, aqueous production is equal to aqueous outflow and intraocular pressure remains fairly constant in the 15 to 21 mmHg range. In glaucoma, the resistance through the canalicular outflow system is abnormally high.

In primary open angle glaucoma, which is the most common form of glaucoma, the abnormal resistance is believed to be along the outer aspect of trabecular meshwork and the inner wall of Schlemm's canal. It is believed that an abnormal metabolism of the trabecular cells leads to an excessive build up of extracellular materials or a build up of abnormally "stiff" materials in this area. Primary open angle glaucoma accounts for approximately eighty-five percent of all glaucoma. Other forms of glaucoma (such as angle closure glaucoma and secondary glaucomas) also involve decreased outflow through the canalicular pathway but the increased resistance is from other causes such as mechanical blockage, inflammatory debris, cellular blockage, etc.

With the increased resistance, the aqueous fluid builds up because it cannot exit fast enough. As the fluid builds up, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to IOP than other eyes. While research is investigating ways to protect the nerve from an elevated pressure, the only therapeutic approach currently available in glaucoma is to reduce the intraocular pressure.

The clinical treatment of glaucoma is approached in a step-wise fashion. Medication often is the first treatment option. Administered either topically or orally, these medications work to either reduce aqueous production or they act to increase outflow. Currently available medications have many serious side effects including: congestive heart failure, respiratory distress, hypertension, depression, renal stones, aplastic anemia, sexual dysfunction and death. Compliance with medication is a major problem, with estimates that over half of glaucoma patients do not follow their correct dosing schedules.

When medication fails to adequately reduce the pressure, laser trabeculoplasty often is performed. In laser trabeculoplasty, thermal energy from a laser is applied to a number of noncontiguous spots in the trabecular meshwork. It is believed that the laser energy stimulates the metabolism of the trabecular cells in some way, and changes the extracellular material in the trabecular meshwork. In approximately eighty percent of patients, aqueous outflow is enhanced and IOP decreases. However, the effect often is not long lasting and fifty percent of patients develop an elevated pressure within five years. The laser surgery is not usually repeatable. In addition, laser trabeculoplasty is not an effective treatment for primary open angle glaucoma in patients less than fifty years of age, nor is it effective for angle closure glaucoma and many secondary glaucomas.

If laser trabeculoplasty does not reduce the pressure enough, then filtering surgery is performed. With filtering surgery, a hole is made in the sclera and angle region. This hole allows the aqueous fluid to leave the eye through an alternate route.

The most commonly performed filtering procedure is a trabeculectomy. In a trabeculectomy, a posterior incision is made in the conjunctiva, the transparent tissue that covers the sclera. The conjunctiva is rolled forward, exposing the sclera at the limbus. A partial thickness scleral flap is made and dissected half-thickness into the cornea. The anterior chamber is entered beneath the scleral flap and a section of deep sclera and trabecular meshwork is excised. The scleral flap is loosely sewn back into place. The conjunctival incision is tightly closed. Post-operatively, the aqueous fluid passes through the hole, beneath the scleral flap and collects in an elevated space beneath the conjunctiva. The fluid then is either absorbed through blood vessels in the conjunctiva or traverses across the conjunctiva into the tear film.

Trabeculectomy is associated with many problems. Fibroblasts that are present in the episclera proliferate and migrate and can sear down the scleral flap. Failure from scarring may occur, particularly in children and young adults. Of eyes that have an initially successful trabeculectomy, eighty percent will fail from scarring within three to five years after surgery. To minimize fibrosis, surgeons now are applying antifibrotic agents such as mitomycin C (MMC) and 5-fluorouracil (5-FU) to the scleral flap at the time of surgery. The use of these agents has increased the success rate of trabeculectomy but also has increased the prevalence of hypotony. Hypotony is a problem that develops when aqueous flows out of the eye too fast. The eye pressure drops too low (usually less than 6.0 mmHg); the structure of the eye collapses and vision decreases.

Trabeculectomy creates a pathway for aqueous fluid to escape to the surface of the eye. At the same time, it creates a pathway for bacteria that normally live on the surface of the eye and eyelids to get into the eye. If this happens, an internal eye infection can occur called endophthalmitis. Endophthalmitis often leads to permanent and profound visual loss. Endophthalmitis can occur anytime after trabeculectomy. The risk increases with the thin blebs that develop after MMC and 5-FU. Another factor that contributes to infection is the placement of a bleb. Eyes that have trabeculectomy performed inferiorly have about five times the risk of eye infection than eyes that have a superior bleb. Therefore, initial trabeculectomy is performed superiorly under the eyelid, in either the nasal or temporal quadrant.

In addition to scarring, hypotony and infection, there are other complications of trabeculectomy. The bleb can tear and lead to profound hypotony. The bleb can be irritating and can disrupt the normal tear film, leading to blurred vision. Patients with blebs generally cannot wear contact lenses. All of the complications from trabeculectomy stem from the fact that fluid is being diverted from inside the eye to the external surface of the eye.

When trabeculectomy doesn't successfully lower the eye pressure, the next surgical step often is an aqueous shunt device. An aqueous diversion device of the prior art is a silicone tube that is attached at one end to a plastic (polypropylene or other synthetic) plate. With an aqueous shunt device, an incision is made in the conjunctiva, exposing the sclera. The plastic plate is sewn to the surface of the eye posteriorly, usually over the equator. A full thickness hole is made into the eye at the limbus, usually with a needle. The tube is inserted into the eye through this hole. The external portion of the tube is covered with either donor sclera or pericardium. The conjunctiva is replaced and the incision is closed tightly.

With prior art aqueous diversion devices, aqueous drains out of the eye through the silicone tube to the surface of the eye. Deeper orbital tissues then absorb the fluid. The outside end of the tube is protected from fibroblasts and scarring by the plastic plate. Many complications are associated with aqueous shunt devices. A thickened wall of scar tissue that develops around the plastic plate offers some resistance to outflow and in many eyes limits the reduction in eye pressure. In some eyes, hypotony develops because the flow through the tube is not restricted. Many physicians tie an absorbable suture around the tube and wait for the suture to dissolve post-operatively at which time enough scar tissue has hopefully formed around the plate. Some devices contain a pressure-sensitive valve within the tube, although these valves may not function properly. The surgery involves operating in the posterior orbit and many patients develop an eye muscle imbalance and double vision post-operatively. With prior art aqueous shunt devices, a pathway is created for bacteria to get into the eye and endophthalmitis can potentially occur.

The prior art includes a number of such aqueous shunt devices, such as U.S. Pat. No. 4,936,825 (providing a tubular shunt from the anterior chamber to the corneal surface for the treatment of glaucoma), U.S. Pat. No. 5,127,901 (directed to a transscleral shunt from the anterior chamber to the subconjunctival space), U.S. Pat. No. 5,180,362 (teaching a helical steel implant that is placed to provide drainage from the anterior chamber to the subconjunctival space), and U.S. Pat. No. 5,433,701 (generally teaching shunting from the anterior chamber to the scleral or conjunctival spaces).

In addition to the prior art aqueous shunt devices described above, other prior art devices for glaucoma surgery have used setons, or other porous, wick-like components to divert and convey excess aqueous from the anterior chamber to the exterior ocular surface. Examples include U.S. Pat. Nos. 4,634,418 and 4,787,885 (teaching the surgical treatment of glaucoma using an implant that consists of a triangular seton (wick)), and U.S. Pat. No. 4,946,436, (teaching the use of a porous device to shunt anterior chamber to subscleral space). These patents do not teach placement in Schlemm's canal.

Some prior art references for glaucoma management have been directed at Schlemm's canal, but these have not involved the placement of long-term, indwelling shunts. U.S. Pat. No. 5,360,399 teaches the temporary placement of a plastic or steel tube with preformed curvature in Schlemm's canal with injection of a viscous material through the tube to hydraulically expand and hydrodissect the trabecular meshwork. The tube is removed from the canal following injection. Because the tube is directed outwardly from the eye for injection access, the intersection of the outflow element with the preformed curved element within Schlemm's canal is at about a 90 degree angle relative to the plane of the curvature, and 180 degrees away from the anterior chamber. Therefore, at no time does any portion of the '399 device communicate with the anterior chamber. Furthermore, relative to that portion within Schlemm's canal, this tube has a larger diameter injection cuff element, which serves as an adapter for irrigation. Therefore, this device is not adapted for shunting aqueous between the anterior chamber and Schlemm's canal.

Most of the problems that have developed with current glaucoma treatment devices and procedures have occurred because aqueous fluid is drained from inside of the eye to the surface of the eye. A need exists, then, for a more physiologic system to enhance the drainage of aqueous fluid from the anterior chamber into Schlemm's canal. In the vast majority of glaucoma patients, the resistance problem lies between Schlemm's canal and the anterior chamber. The canal itself, the collecting channels and the episcleral venous system all are intact. Enhancing aqueous flow directly into Schlemm's canal would minimize the scarring that usually occurs with external filtration procedure since the internal angle region is populated with a single line of nonproliferating trabecular cells. Enhancing aqueous flow directly into Schlemm's canal would minimize hypotony since the canal is part of the normal outflow system and is biologically engineered to handle the normal volume of aqueous humor. Enhancing aqueous flow directly into Schlemm's canal would eliminate complications such as endophthalmitis and leaks.

SUMMARY OF THE INVENTION

The present invention is directed to a novel shunt and an associated surgical method for the treatment of glaucoma in which the shunt is placed to divert aqueous humor from the anterior chamber of the eye into Schlemm's canal. The present invention therefore facilitates the normal physiologic pathway for drainage of aqueous humor from the anterior chamber, rather than shunting to the sclera or another anatomic site as is done in most prior art shunt devices. The present invention is further directed to providing a permanent, indwelling shunt to provide increased egress of aqueous humor from the anterior chamber to Schlemm's canal for glaucoma management.

BRIEF DESCRIPTION OF THE DRAWINGS

FIG. 1A is an illustration showing an overhead perspective view of one embodiment of the present invention, in which the inventive shunt is comprised of tubular elements extending bi-directionally within Schlemm's canal.

FIG. 1B is an overhead view of the embodiment of the present invention shown in FIG. 1A, with phantom lines detailing the internal communication between the lumens of the tubular elements comprising the inventive device.

FIG. 1C is an illustration showing an overhead perspective view of one embodiment of the present invention, in which the inventive shunt is comprised of mesh tubular elements extending bi-directionally within Schlemm's canal.

FIG. 1D is an illustration showing an overhead perspective view of one embodiment of the present invention, in which the inventive shunt is comprised of solid, porous elements extending bi-directionally within Schlemm's canal.

DETAILED DESCRIPTION OF PRESENT INVENTION

Figure 1E:
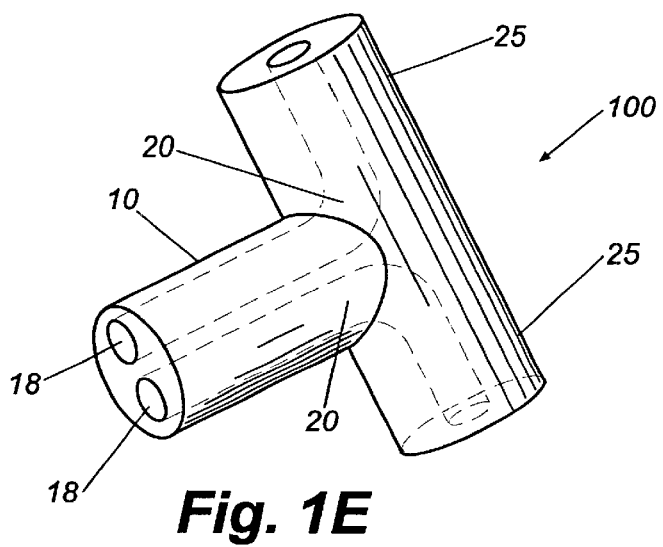
FIG. 1E is an overhead perspective view of another embodiment of the present invention, with phantom lines detailing the internal communication between the two proximal lumens and the single distal lumen of the inventive device.

The present invention provides an aqueous humor shunt device to divert aqueous humor in the eye from the anterior chamber into Schlemm's canal, in which the shunt device comprises a distal portion having at least one terminal aspect sized and shaped to be circumferentially received within a portion of Schlemm's canal, and a proximal portion having at least one terminal aspect sized and shaped to be received within the anterior chamber of the eye, wherein the device permits fluid communication between the proximal portion in the anterior chamber to the distal portion in Schlemm's canal. Fluid communication can be facilitated by an aqueous humor directing channel in either the proximal or distal portions, as described below. Fluid communication can also be facilitated by a wicking function of a solid proximal or distal portions of the device, for example.

The present invention also provides embodiments of an inventive shunt comprising a body of biocompatible material of a size and shape adapted to be at least partially circumferentially received within a portion of Schlemm's canal to divert aqueous humor from the anterior chamber of the human eye to and within Schlemm's canal, and wherein the body facilitates the passage of aqueous humor from the anterior chamber into Schlemm's canal. This embodiment of the device of the present invention can be produced without the proximal portion of the previous embodiment extending into the anterior chamber. An aqueous humor directing channel can facilitate the passage of aqueous humor from the anterior chamber into Schlemm's canal. Fluid communication can also be facilitated by a wicking function of a solid body portion, for example.

The invention contemplates many different configurations for an aqueous humor directing channel, provided that each assists in channeling aqueous humor from the anterior chamber to Schlemm's canal, such as by providing a lumen, trough, wick or capillary action. For example, the aqueous humor directing channel can be a fully enclosed lumen, a partially enclosed lumen, or a trough-like channel that is at least partially open. The invention contemplates that a solid monofilament or braided polymer, such as proline, can be inserted into Schlemm's canal to provide a wicking function to facilitate the passage of aqueous humor from the anterior chamber to Schlemm's canal. Such a wicking extension can also be grooved or fluted along any portion of the length thereof, so as to be multi-angular or star-shaped in cross-section. The devices of the present invention can be constructed of a solid, matrix, mesh, fenestrated, or porous material, or combinations thereof.

Traditional glaucoma teaching states that Schlemm's canal in an adult is divided by septa into separate canals, rendering the complete passage of a suture impossible. Preliminary studies on adult human eye bank eyes have shown that Schlemm's canal is, indeed, patent. A suture can be passed through the entire circumference of the canal. It has not been heretofore determined that Schlemm's canal is patent throughout its circumference in normal adult individuals, as opposed to being divided by septae into multiple dead end canals. The invention utilizes this knowledge to access Schlemm's canal and to create and maintain the natural physiologic egress of aqueous humor from the anterior chamber to Schlemm's canal and to the collecting channels.

The present invention also provides methods of use of the shunt devices. One embodiment of the present invention is directed to a surgical method to divert aqueous humor from the anterior chamber of the eye into Schlemm's canal with a device that is implanted to extend from within the anterior chamber to Schlemm's canal. The portion of the device extending into Schlemm's canal can be fashioned from a flexible material capable of being received within a portion of the radius, curvature, and diameter of Schlemm's canal. All or parts of the device may be solid, porous, tubular, trough-like, fenestrated, or pre-curved.

One embodiment of the present invention is illustrated in FIG. 1A, in which the shunt device 100 is shown in a side view. The shunt device 100 of this embodiment is comprised of two portions, a proximal portion 10 which joins a distal portion 25. The proximal portion 10 and distal portion 25 shown create an enclosed tubular channeling structure. The total length of the distal portion 25 may be between about 1 and 40 mm, preferably about 6 mm. The same embodiment of the present invention is illustrated with phantom lines showing the internal fluid communication path in FIG. 1B. The lumen or channeling space defined by the walls of the proximal portion 10 and the distal portion(s) 25 are continuous at their junction at the distal portion portal 20.

An alternate embodiment of the present invention is shown in FIG. 1C, in which the shunt device 100 is comprised of two luminal mesh elements, with a proximal portion 10 which joins a distal portion 25. Yet another embodiment of the present invention is shown in FIG. 1D, in which the shunt device 100 is comprised of two solid, porous elements which may provide wick-like fluid communication therethrough, with a proximal portion 10 which joins a distal portion 25.

An alternate embodiment of the present invention is shown in FIG. 1E, in which the shunt device 100 is comprised of a proximal portion 10 having two lumens therein terminating in proximal portion portals 18. The distal portion 25 shaped and sized to be received within Schlemm's canal extends in either direction having separate lumens traversing therethrough from each of the distal portion portals 20.

Figure 2:
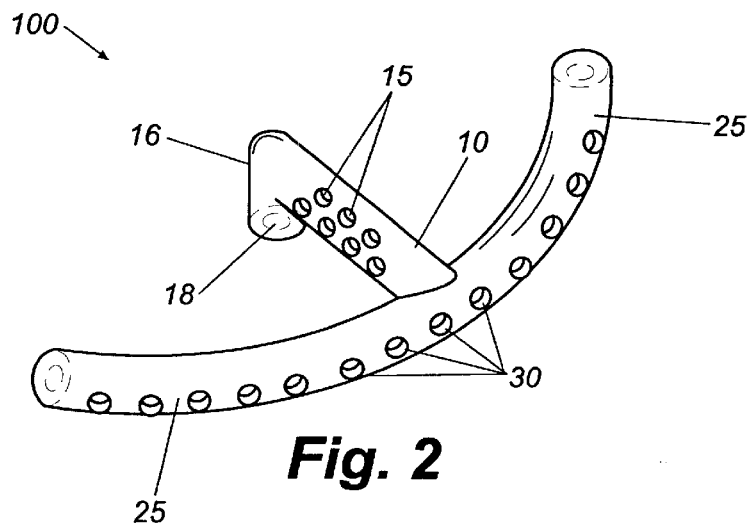
FIG. 2 is an illustration showing another embodiment of the present invention, in which the inventive shunt is comprised of perforated tubular elements and with an angulated terminal aspect of the proximal portion.

Other examples of embodiments of the present invention are shown in FIGS. 2–5D. FIG. 2 shows an embodiment of the inventive shunt in which the device 100 is tubular and fenestrated (15, 30) in its configuration, with an acute (<90°) angle of junction between the proximal portion 10 and the plane defined by the distal portion 25. Such fenestrations (15, 30) may be placed along any portion of the device 100 to facilitate the passage of fluid therethrough, but are particularly directed towards the collecting channels of the eye. FIG. 2 further shows an alternate embodiment of the present invention in which the terminal aspect 16 of the proximal portion is angulated toward the iris 40 with respect to the main axis of the proximal portion 10, with the portal 18 of the proximal portion directed toward the iris 40. In alternate embodiments as shown in FIG. 6C, the portal 18 of the proximal portion 16 is directed away from the iris 40.

Figure 3A:
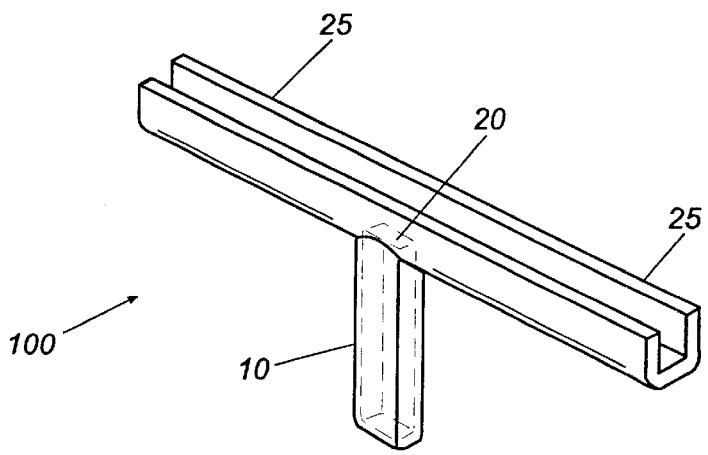
FIG. 3A is an illustration showing a perspective of another embodiment of the present invention in which the inventive shunt is comprised of elements that are partially tubular and partially open in their configuration.

FIG. 3A shows an embodiment of the inventive shunt in which a portion of the channeling device is enclosed and tubular in configuration at the junction of the proximal portion 10 and the distal portion 25, but where the distal portion 10 is a trough-like channel. The distal portion portal 20 is also shown. The invention contemplates that any portion of the device 100 can be semi-tubular, open and trough-like, or a wick-like extension. Tubular channels can be round, ovoid, or any other enclosed geometry. Preferably the non-tubular trough-like aspects are oriented posteriorly on the outer wall of the canal to facilitate aqueous humor drainage to the collecting channels of the eye, as shown in FIG. 3A.

Figure 3B:
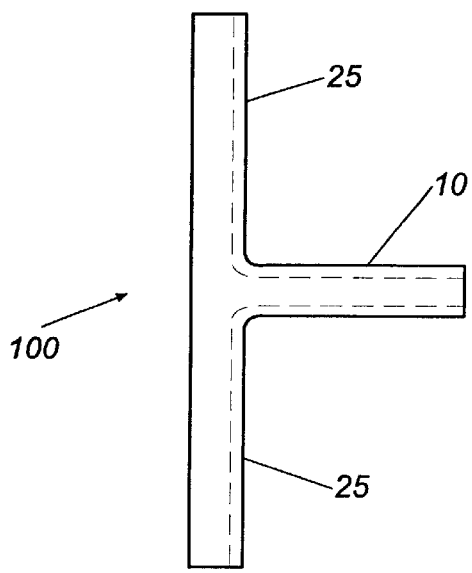
FIG. 3B is an illustration showing a top view of the embodiment of the present invention in FIG. 3A, with phantom lines detailing the internal communication of the device.
Figure 3C:
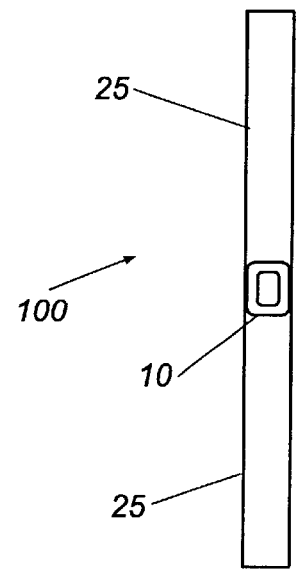
FIG. 3C is an illustration showing a side view from the proximal end of the embodiment of the present invention in FIG. 3A.

FIG. 3B shows an overhead view of the embodiment of the inventive shunt of FIG. 3A, further detailing the relationship among the proximal portion 10 and the distal portion 25. The aqueous humor directing channel is shown in dashed lines. FIG. 3C shows a proximal view of the embodiment of the inventive shunt of FIG. 3A, further detailing the relationship among the proximal portion 10 and the distal portion 25.

Figure 3D:
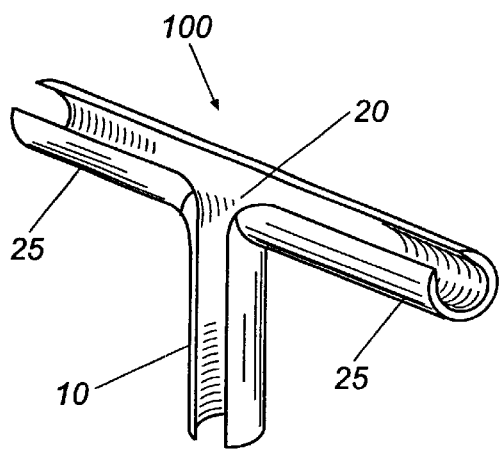
FIG. 3D is an illustration showing a perspective of another embodiment of the present invention in which the inventive shunt is comprised of elements that are partially open and trough-like in their configuration.

FIG. 3D shows another embodiment of the inventive shunt in which the structure of the device 100 comprises an aqueous humor directing channel that is both open and curved in a continuous trough-like configuration along the proximal portion 10 and the distal portion 25. The distal portion portal 20 is also an open trough-like channel.

Figure 4:
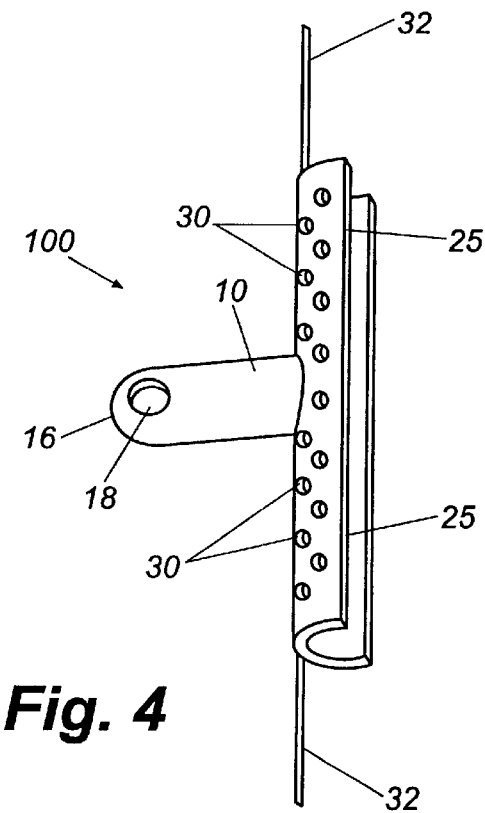
FIG. 4 is an illustration showing another embodiment of the present invention, in which the inventive shunt is comprised of distal elements having wicking extensions at their terminal ends, and in which the proximal portion has a sealed, blunted tip with a portal continuous with the lumen of the proximal portion, oriented to face away from the iris when the device is implanted in Schlemm's canal.

FIG. 4 shows another embodiment of the inventive shunt with the addition of aqueous humor-wicking extensions 32 which are either continuous with, or attached to the terminal aspects of the distal portion 25. The wicking extensions 32 can be fashioned from a monofilament or braided polymer, such as proline, and preferably have a length of 1.0 mm to 16.0 mm. Furthermore, the proximal portion 10 is curved with a sealed, blunted tip 16 and contains a portal 18 in fluid communication with the lumen of the proximal portion and oriented to face away from the iris when the shunt device 100 is implanted in its intended anatomic position. The shunt device 100 can also help to maintain the patency of Schlemm's canal in a stenting fashion.

Figure 5A:
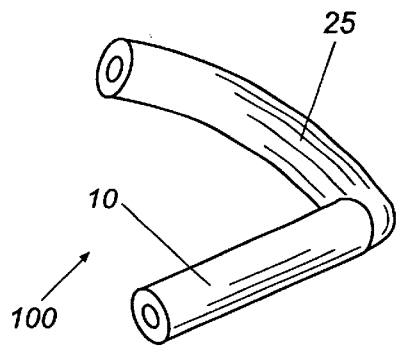
FIG. 5A is an illustration showing another embodiment of the inventive shunt in which a portion of the device enters Schlemm's canal in only one direction and shunts fluid in a non-linear path from the anterior chamber.

FIG. 5A shows another embodiment of the inventive shunt in which the proximal portion 10 joins a single, curved distal portion 25 in a "V-shaped," tubular configuration. The embodiment shown in FIG. 5A can also have a portal (not shown) in the distal portion 25 adjacent to the junction with the proximal portion 10 in order to facilitate bi-directional flow of fluid within the canal. Fenestrations and non-tubular, trough-like terminal openings are contemplated in all embodiments of the invention, and these fenestrations and openings may be round, ovoid, or other shapes as needed for optimum aqueous humor channeling function within the anatomic spaces involved.

Figure 5B:
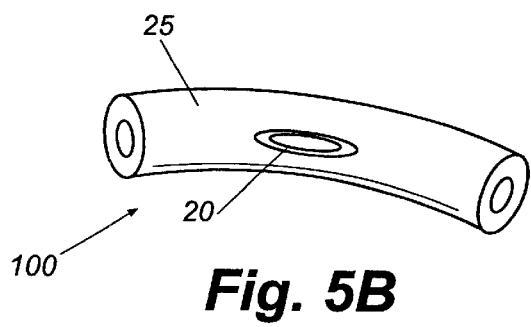
FIG. 5B is an illustration showing an alternative embodiment of the inventive shunt in which the entire shunt is placed within Schlemm's canal but contains a fenestration to maintain fluid egress of aqueous humor from the anterior chamber to Schlemm's canal.

FIG. 5B shows another embodiment of the inventive shunt in which the body or device 100 comprises only a single, curved distal portion 25 which contains a distal portion portal 20 oriented towards the anterior chamber to allow egress of aqueous humor from the anterior chamber to Schlemm's canal. The body of this device can have a length of about 1.0 mm to 40 mm, preferably about 6 mm. The external diameter can be about 0.1 mm to 0.5 mm, or about 0.3 mm.

Figure 5C:
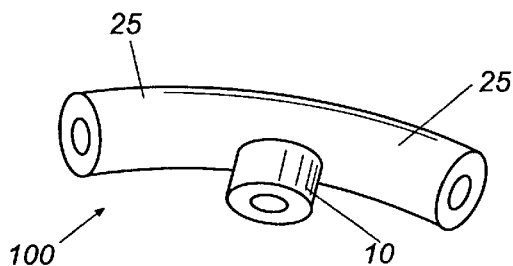
FIG. 5C is an illustration showing a side view of one embodiment of the present invention, in which the inventive shunt is comprised of tubular elements, with a proximal portion extending towards the anterior chamber that is shorter relative to the distal portions which extend bi-directionally within Schlemm's canal.

FIG. 5C shows another embodiment of the inventive shunt in which the device 100 comprises a bidirectional tubular distal portion 25 which is intersected by a proximal portion 10 which is short in length relative to the distal portion 25 and is directed towards the anterior chamber.

Figure 5D:
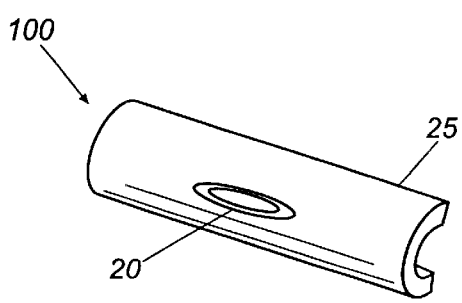
FIG. 5D is an illustration showing an alternative embodiment of the inventive shunt comprised of a partially open troughlike element which is placed within Schlemm's canal but contains a portal to maintain fluid egress of aqueous humor from the anterior chamber to Schlemm's canal.

FIG. 5D shows still another embodiment of the inventive shunt in which the device 100 comprises a bi-directional, trough-like, curved distal portion 25 for insertion into Schlemm's canal, which contains a distal portion portal 20 oriented to allow egress of aqueous humor from the anterior chamber, wherein the trough-like distal portion 25 is oriented to open toward the collecting channels to facilitate the egress of aqueous humor.

Figure 5E:
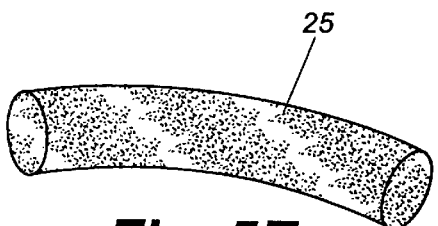
FIG. 5E is an illustration showing an alternative embodiment of the inventive shunt comprised of a solid, but porous wicklike element which is placed within Schlemm's canal

FIG. 5E shows another embodiment of the inventive shunt in which the device 100 comprises a bidirectional, solid distal portion 25 for insertion into Schlemm's canal to facilitate the egress of aqueous humor from the canal to the collecting channels in a wicking capacity. The solid distal portion 25 can be porous or non-porous.

As the inventive device is an implant, it can be fabricated from a material that will be compatible with the tissues and fluids with which it is in contact. It is preferable that the device not be absorbed, corroded, or otherwise structurally compromised during its in situ tenure. Moreover, it is equally important that the eye tissues and the aqueous remain non-detrimentally affected by the presence of the implanted device. A number of materials are available to meet the engineering and medical specifications for the shunts. In the exemplary embodiments of the present invention, the shunt device 100 is constructed of a biologically inert, flexible material such as silicone or similar polymers. Alternate materials might include, but are not limited to, thin-walled Teflon, polypropylene, other polymers or plastics, metals, or some combination of these materials. The shunt device 100 may be constructed as either porous or solid in alternate embodiments. The material can contain a therapeutic agent deliverable to the adjacent tissues.

In the embodiments shown in FIGS. 1–4, the proximal portion 10 joins the distal portion(s) 25 at an angle sufficient to allow the placement of the proximal portion 15 within the anterior chamber of the eye when the distal portion 25 is oriented in the plane of Schlemm's canal. The proximal portion 10 is preferably of sufficient length, about 0.1 to 3.0 mm or about 2.0 mm, to extend from its junction with the distal portion 25 in Schlemm's canal towards the adjacent space of the anterior chamber. While many geometries can be used for channeling aqueous humor, the diameter or width of the proximal portion 10 can be sized to yield an internal diameter of between about 0.1 and 0.5 mm, preferably 0.20 mm for a tubular or curved shunt, or a comparable maximal width for a shunt with a multiangular configuration. In other embodiments, the proximal portion is a non-luminal, non-trough-like wicking extension that provides an aqueous humor directing channel along the length thereof.

Because the nature of the iris 40 is such that it tends to comprise a plurality of rather flaccid fimbriae of tissue, it is desirable to avoid said fimbriae from being drawn into the lumen of an implant, thus occluding the shunt device. Therefore, the proximal portion 10 may contain a plurality of fenestrations to allow fluid ingress, arranged to prevent occlusion by the adjacent iris. Alternately, the proximal portion 10 may comprise only a proximal portion portal 18 in the form of a fenestration oriented anteriorly to provide continuous fluid egress between the anterior chamber of the eye and the directing channel of the shunt. Said fenestrations may be any functional size, and circular or noncircular in various embodiments of the present invention. In addition, a porous structural material can assist in channeling aqueous humor, while minimizing the potential for intake of fimbriae.

Furthermore, the proximal portion 10 may be positioned sufficiently remote from the iris 40 to prevent interference therewith, such as by traversing a more anterior aspect of the trabecular meshwork into the peripheral corneal tissue. In yet another possible embodiment, as shown in FIG. 6C, the device 100 may comprise a proximal portion 10 in which the terminal aspect of said proximal portion 10 is curved or angled toward the iris 40, and with a blunted, sealed tip 16 and a portal 18 oriented anteriorly to face away from the underlying iris 40. Such a configuration would tend to decrease the possibility of occlusion of the shunt device by the iris 40.

The device 100 may contain one or more unidirectional valves to prevent backflow into the anterior chamber from Schlemm's canal. The internal lumen for an enclosed portion of the device or the internal channel defined by the edges of an open portion of the device communicates directly with the inner lumen or channel of the distal portion at the proximal portion portal 20.

The distal portion 25 may have a pre-formed curve to approximate the 6.0 mm radius of Schlemm's canal in a human eye. Such a pre-formed curvature is not required when flexible material is used to construct the shunt device 100. The distal portion 25 may be of sufficient length to extend from the junction with the proximal portion 10 through any length of the entire circumference of Schlemm's canal. Embodiments having a distal portion 25 that extends in either direction within Schlemm's canal can extend in each direction about 1.0 mm to 20 mm, or about 3.0 mm. to permit circumferential placement through Schlemm's canal. The diameter or width of the distal portion 25 can be sized to yield an outer diameter of between about 0.1 and 0.5 mm, or about 0.3 mm, for a tubular or curved shunt, or a comparable maximal width for a shunt with a multiangular configuration. The distal portion 25 may contain a plurality of fenestrations to allow fluid egress, arranged to prevent occlusion by the adjacent walls of Schlemm's canal. In other embodiments, the distal portion is a non-luminal, non-trough-like wicking extension that provides an aqueous humor directing channel along the length thereof.

In the exemplary embodiments of the present invention, the shunt device may be either bidirectional, with the distal portion of the implant intersecting with the proximal portion in a "T-shaped" junction as shown in FIGS. 1A–1E, 2, 3A–3D, 4 and 5C, or unidirectional, with a "V-shaped" junction of the proximal and distal shunt portions, as shown in FIG. 5A. A bi-directional shunt device can have a distal portion that is threaded into opposing directions within Schlemm's canal. In the case of the unidirectional shunt, only the distal shunt portion is placed within Schlemm's canal. In these exemplary embodiments, "non-linear fluid communication" means that at least some portion of the shunt through which fluid passes is not in a straight line. Examples of non-linear shunts are the above described bidirectional "T" shapes, and the unidirectional "V" shapes, or shunts having two channel openings which are not in straight alignment with each other.

Figure 6A:
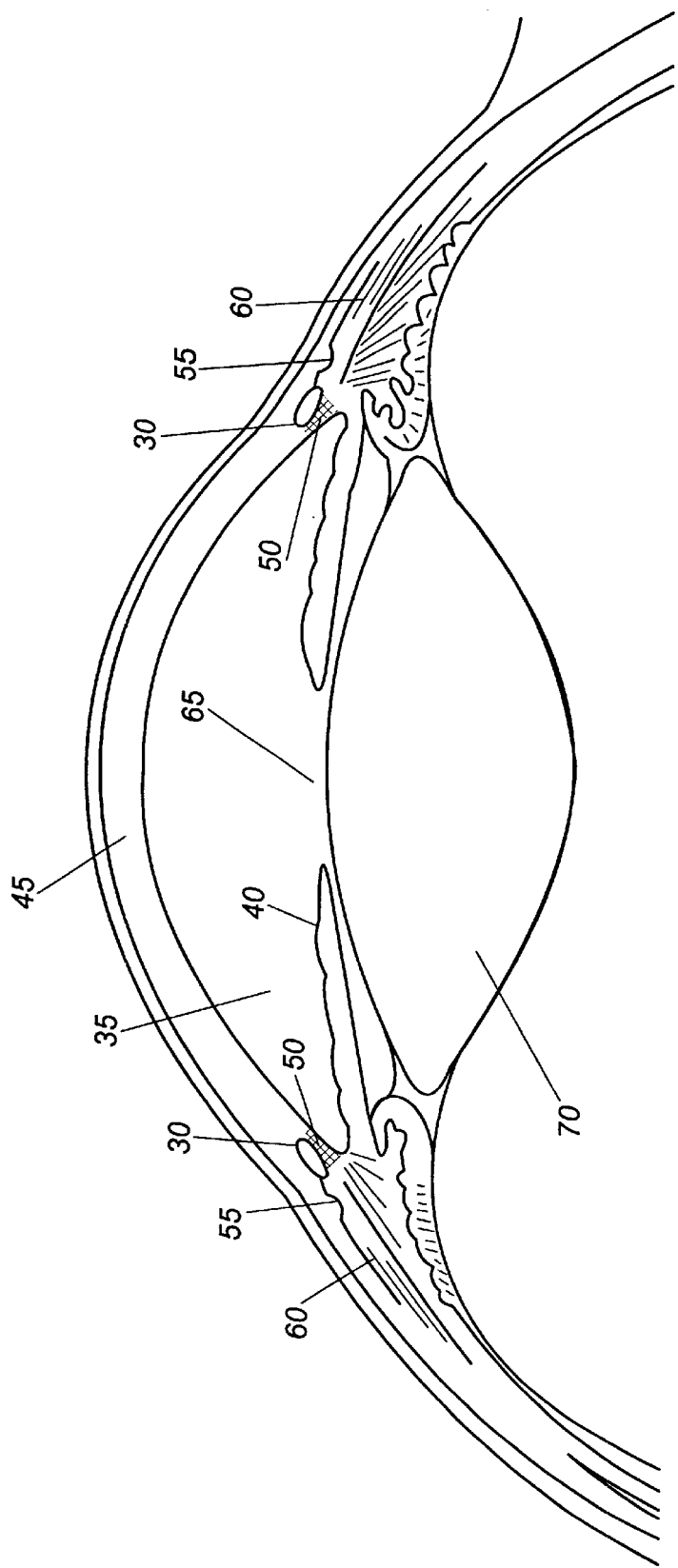
FIG. 6A is an illustration showing certain anatomic details of the human eye.
Figure 6B:
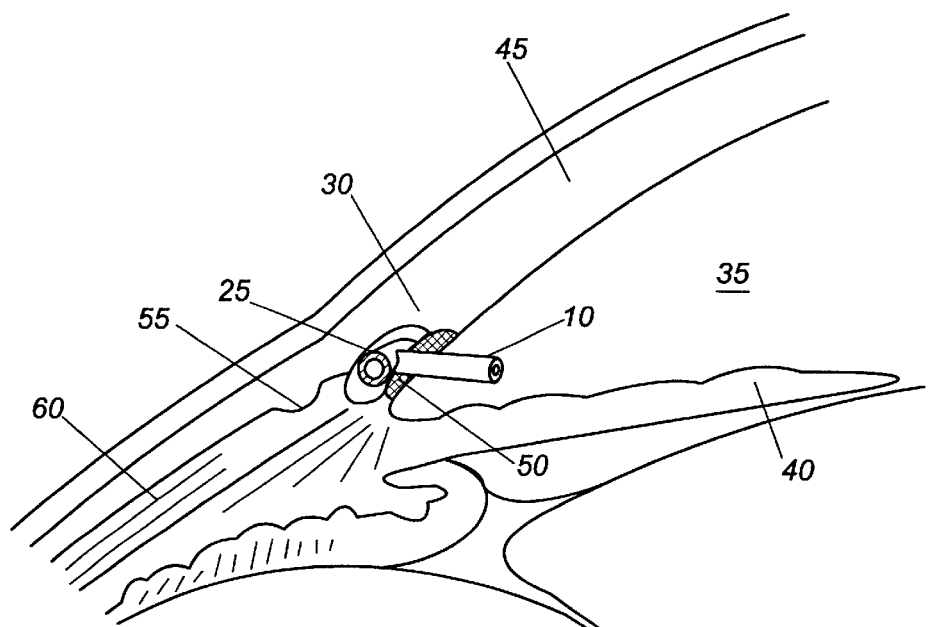
FIG. 6B is a cross-sectional illustration showing the anatomic relationships of the surgical placement of an exemplary embodiment of the present invention.
Figure 6C:
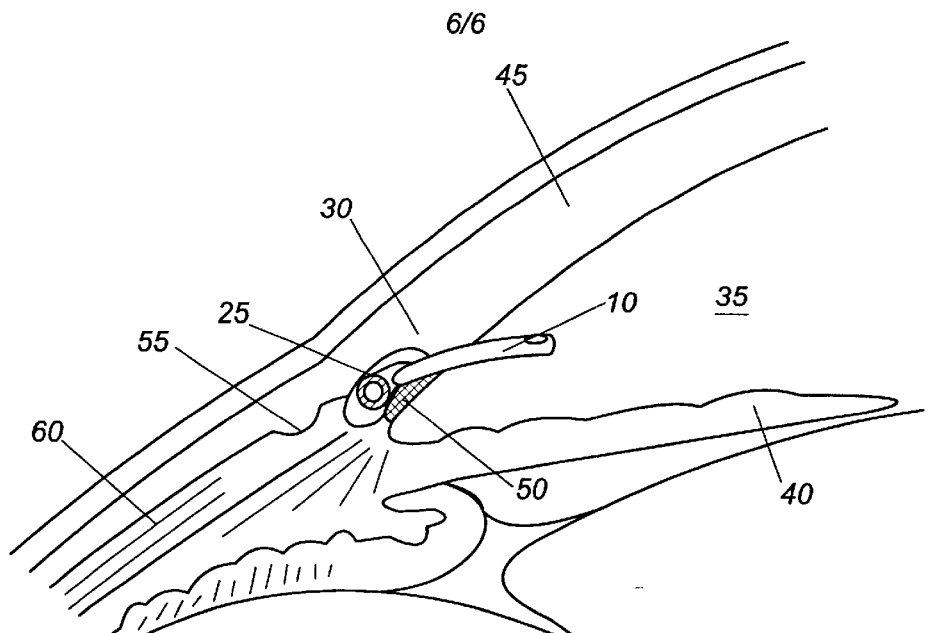
FIG. 6C is a cross-sectional illustration showing the anatomic relationships of the surgical placement of another exemplary embodiment of the present invention in which the proximal portion has an angulated terminal aspect with a sealed, blunted tip with a portal continuous with the lumen of the proximal portion, oriented to face away from the iris when the device is implanted in Schlemm's canal.

The surgical anatomy relevant to the present invention is illustrated in FIG. 6A. Generally, FIG. 6A shows the anterior chamber 35, Schlemm's canal 30, the iris 40, cornea 45, trabecular meshwork 50, collecting channels 55, episcleral veins 60, pupil 65, and lens 70. FIG. 6B illustrates the surgical placement of the exemplary embodiment of the present invention, with the relevant anatomic relationships. It should be noted that the inventive device is designed so that placement of the distal portion 25 within Schlemm's canal 30 results in an orientation of the proximal portion 10 within the anterior chamber 35 within the angle defined by the iris 40 and the inner surface of the cornea 45. Therefore, if the plane defined by Schlemm's canal is defined as zero degrees, the proximal portion 10 can extend therefrom at an angle of between about +60 degrees towards the cornea 45 or −30 degrees toward the iris 40, more preferably in the range of 0 to +45 degrees. This range may vary in individuals having a slightly different location of Schlemm's canal 30 relative to the limbal angle of the anterior chamber 35.

In yet another embodiment of the present invention not shown, the shunt device 100 is configured with one distal portion 25 which is tubular to provide a shunting functionality and a plurality of proximal portions 10 which provide an anchoring function to stabilize the overall implant device, in addition to providing fluid communication from the anterior chamber to Schlemm's Canal.

The surgical procedure necessary to insert the device requires an approach through a conjunctival flap. A partial thickness scleral flap is then created and dissected half-thickness into clear cornea. The posterior aspect of Schlemm's canal is identified and the canal is entered posteriorly. The anterior chamber may be deepened with injection of a viscoelastic and a miotic agent. The proximal portion of the shunt is then inserted through the inner wall of Schlemm's canal and trabecular meshwork into the anterior chamber within the angle between the iris and the cornea. In some cases, as incision may be needed from Schlemm's canal through the trabecular meshwork into the anterior chamber to facilitate passage of the proximal portion therethrough. One arm of the distal portion of the shunt device is grasped and threaded into Schlemm's canal. In a similar fashion, the other arm of the distal portion of the shunt device (when present) is inserted into Schlemm's canal in the opposing direction from the first. The scleral flap and conjunctival wound are closed in a conventional manner.

While the above-described embodiments are exemplary, the invention contemplates a wide variety of shapes and configurations of the shunt to provide fluid communication between the anterior chamber and Schlemm's canal. The above-described embodiments are therefore not intended to be limiting to the scope of the claims and equivalents thereof.

What is claimed is:

1. An aqueous humor shunt device to divert aqueous humor in an eye from the anterior chamber into Schlemm's canal, the shunt device comprising a distal portion having at least one terminal aspect sized and shaped to be received circumferentially within a portion of Schlemm's canal and a proximal portion having at least one terminal aspect sized and shaped to be received within the anterior chamber of the eye, wherein device permits fluid communication from the proximal portion in the anterior chamber to the distal portion in Schlemm's canal.

2. The shunt device of claim 1, wherein the distal portion of the shunt has a curve having a radius which approximates the radius of Schlemm's canal of a human eye.

3. The shunt device of claim 2, wherein said curve has a radius of between about 3 mm and 10 mm.

4. The shunt device of claim 2, wherein said curve has a radius of about 6 mm.

5. The shunt device of claim 1, wherein the proximal portion of the shunt intersects the distal portion and wherein the distal portion branches in two opposite directions from the intersection with the proximal portion permitting fluid communication from the anterior chamber in either direction along Schlemm's canal.

6. The shunt device of claim 5, wherein the proximal portion of the shunt intersects the distal portion at about the midpoint of the length of the distal portion.

7. The shunt device of claim 1, wherein the distal portion extends in one direction within Schlemm's canal.

8. The shunt device of claim 1, wherein the proximal portion extends from the distal portion at an angle to avoid occlusion from contact with corneal endothelium tissue or iris tissue when the distal portion is located within Schlemm's canal.

9. The surgical device of claim 1, wherein said distal portion has an outer diameter of about 0.1 mm to 0.5 mm.

10. The shunt device of claim 1, wherein said distal portion has an outer diameter of about 0.30 mm.

11. The shunt device of claim 1, wherein said proximal portion is tubular having a lumen with an internal diameter of between about 0.1 mm and 0.5 mm.

12. The shunt device of claim 1, wherein said proximal portion is tubular with a lumen with an internal diameter of about 0.2 mm.

13. The shunt device of claim 1, wherein said proximal portion has a length of about 0.1 to 3 mm.

14. The shunt device of claim 1, wherein said proximal portion has a length of about 2 mm.

15. The shunt device of claim 1, wherein said distal portion has a length of about 1 mm to 20 mm.

16. The shunt device of claim 1, wherein said distal portion has a length of about 6 mm.

17. The shunt device of claim 1, where the distal portion has a lumen therethrough that allows the passage of fluid into Schlemm's canal.

18. The shunt device of claim 1, where the distal portion has a plurality of fenestrations therein that allow the passage of fluid into Schlemm's canal.

19. The shunt device of claim 1, where the proximal portion has a lumen therethrough that facilitates the passage of fluid into the distal portion of the shunt.

20. The shunt device of claim 1, where the proximal portion has two lumens therethrough that facilitates the passage of fluid into the distal portion of the shunt in opposite directions.

21. The shunt device of claim 1, where the proximal portion has a plurality of fenestrations therein that facilitate the passage of fluid into the distal portion of the shunt.

22. The shunt device of claim 21, wherein the lumen of the proximal portion communicates with one or more fenestrations oriented to open towards the inner surface of the cornea and away from the iris.

23. The shunt device of claim 1, further comprising a plurality of proximal portions intersecting the distal portion.

24. The shunt device of claim 1, in which an aqueous humor wicking extension of between about 1.0 mm to 16.0 mm in length extends from said terminal aspect of the distal portion.

25. The shunt device of claim 1, wherein at least a portion of the distal portion is a partially open trough-like channel open posteriorly toward the collecting channels of the eye.

26. The shunt device of claim 1, wherein at least a portion of the device is constructed from porous material.

27. The shunt device of claim 1, in which the terminal aspect of the proximal portion is angled internally towards the anterior chamber with respect to the proximal portion.

28. A method for the surgical treatment of glaucoma, comprising, performing a trabeculotomy through a conjunctival flap made at the limbus; developing a partial thickness scleral flap; radially incising the junction between the angle tissue and the sclera, which is surgically extended until Schlemm's canal is entered posteriorly, and placing the shunt device of claim 1 between the anterior chamber and Schlemm's canal.

29. An aqueous humor shunt device for use in an eye to relieve intraocular pressure by facilitating drainage from the anterior chamber of the eye into Schlemm's canal, comprising:

a body of biocompatible material of a size and shape adapted to facilitate the passage of aqueous humor from the anterior chamber of the eye to and within Schlemm's canal;

said body having a length and shape adapted to be at least partially circumferentially retained within a portion of Schlemm's canal to facilitate the passage of aqueous humor from the anterior chamber to Schlemm's canal.

30. The shunt device of claim 29, wherein the body of the shunt has a curve having a radius which approximates the radius of Schlemm's canal of a human eye.

31. The shunt device of claim 30, wherein said curve has a radius of between about 3 mm and 10 mm.

32. The shunt device of claim 31, wherein said curve has a radius of about 6 mm.

33. The shunt device of claim 29, wherein the body has a proximal portion having at least one terminal aspect for placement within the anterior chamber and a distal portion having at least one terminal aspect for placement within Schlemm's canal.

34. The shunt device of claim 33, wherein the proximal portion intersects the distal portion and wherein the distal portion branches in two opposite directions from the intersection with the proximal portion permitting fluid communication in either direction along Schlemm's canal with the anterior chamber.

35. The shunt device of claim 34, wherein the proximal portion intersects the distal portion at or near the midpoint of the length of the distal portion.

36. The shunt device of claim 33, wherein the proximal portion extends from the distal portion at an angle sufficient to avoid occlusion from contact with corneal endothelium tissue or iris tissue when the distal portion is located within Schlemm's canal.

37. The shunt device of claim 29, wherein the body defines a tubular channel along at least some of the length of said body.

38. The shunt device of claim 29, wherein said body is tubular and has an outer diameter of about 0.1 mm to 0.5 mm.

39. The shunt device of claim 29, wherein said body is tubular and has an outer diameter of about 0.3 mm.

40. The shunt device of claim 29, wherein said body has a length of about 1 mm to 20 mm.

41. The shunt device of claim 29, wherein said body has a length of about 6 mm.

42. The shunt device of claim 29, in which an aqueous humor wicking extension of between about 1.0 mm to 16.0 mm in length extends from said body.

43. The shunt device of claim 29, wherein the body defines a partially open trough-like channel open toward the collecting channels along at least some of the length of said body.

44. The shunt device of claim 29, wherein the body is fenestrated to provide communication with the lumen along at least some of the length of said body.

45. The shunt device of claim 29, wherein the body provides for drainage in one direction along Schlemm's canal.

46. The shunt device of claim 29, wherein the body provides for drainage in both directions along Schlemm's canal.

47. A method for the surgical treatment of glaucoma, comprising, performing a trabeculotomy through a conjunctival flap made at the limbus; developing a partial thickness scleral flap; radially incising the junction between the angle tissue and the sclera, which is surgically extended until Schlemm's canal is entered posteriorly, and placing the shunt device of claim 29 between the anterior chamber and Schlemm's canal.

\* \* \* \* \*

UNITED STATES PATENT AND TRADEMARK OFFICE
CERTIFICATE OF CORRECTION

PATENT NO. : 6,450,984 B1
DATED : September 17, 2002
INVENTOR(S) : Lynch et al.

It is certified that error appears in the above-identified patent and that said Letters Patent is hereby corrected as shown below:

<u>Title page</u>,
Item [60], Related U.S. Application Data, please add the following government license:

-- Government License
  The U.S. Government has reserved a nonexclusive, irrevocable, royalty-free license in the invention with power to grant licenses for all government purposes. --

Signed and Sealed this

Twelfth Day of October, 2004

JON W. DUDAS
*Director of the United States Patent and Trademark Office*